United States Patent
Salimbeni et al.

Patent Number: 5,565,464
Date of Patent: Oct. 15, 1996

[54] COMPOUNDS HAVING ANGIOTENSINE II ANTAGONISTIC ACTIVITY

[75] Inventors: Aldo Salimbeni; Davide Poma; Elso Manghisi; Carlo Scolastico, all of Milan, Italy

[73] Assignee: Istituto Luso Farmaco d'Italia S.p.A., Milan, Italy

[21] Appl. No.: 193,025

[22] PCT Filed: Aug. 3, 1992

[86] PCT No.: PCT/EP92/01753

§ 371 Date: Mar. 21, 1994

§ 102(e) Date: Mar. 21, 1994

[87] PCT Pub. No.: WO93/03018

PCT Pub. Date: Feb. 18, 1993

[30] Foreign Application Priority Data

Aug. 2, 1991 [IT] Italy .................. MI91A2182

[51] Int. Cl.⁶ .................. C07D 401/10; A61K 31/505
[52] U.S. Cl. .................. 514/269; 514/272; 514/274; 544/310; 544/316; 544/319; 544/321
[58] Field of Search .................. 544/319, 320, 544/321, 310, 316; 514/269, 272, 274

[56] References Cited

U.S. PATENT DOCUMENTS 5,166,206  11/1992  Allen ................ 544/330

FOREIGN PATENT DOCUMENTS 424317  4/1991  European Pat. Off. ..
435827  4/1991  European Pat. Off. ..

*Primary Examiner*—John M. Ford
*Attorney, Agent, or Firm*—Bucknam and Archer

[57] ABSTRACT

Compounds having a angiotensine II antagonistic activity

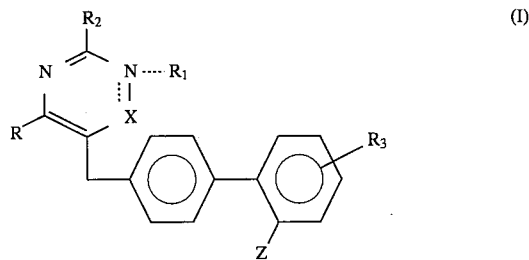

Compounds of formula (I), wherein R, $R_1$, $R_2$, $R_3$, X and Z groups have the meanings given in the specification and are endowed with AII antagonistic properties.

6 Claims, No Drawings

COMPOUNDS HAVING ANGIOTENSINE II ANTAGONISTIC ACTIVITY

This application is a 371 of PCT/EP92/01753, filed Aug. 3, 1992.

FIELD OF THE INVENTION

The present invention refers to heterocyclic compounds having angiotensine II antagonistic activity.

BACKGROUND OF THE INVENTION

The renin-angiotensine system (RAS) is a proteolytic cascade playing a fundamental role in regulating blood pressure and is apparently involved in the onset and maintenance of some cardiovascular pathologies, such as hypertension or heart failure.

The octapeptide hormone angiotensine II (AII) final product of RAS, is mainly formed in blood by the degradation of angiotensine I by the ACE enzyme which is localized in the endothelium of blood vessels, lungs, kidneys and many other organs. This hormone exerts on the arteries a powerful vasoconstrictive action as a consequence of its interaction with specific receptors, present on the cell membranes.

One of the possible control modes of RAS is the AII antagonism at the receptorial level. Some peptide analogues of AII (e.g. saralasine, sarmesine) are known to antagonize competitively the interactions of the hormone, but their clinical or experimental use has been limited by a partial agonist activity and by the lack of oral activity.

Recently, several non-peptide 5-or 6-membered heterocyclic compounds were disclosed as AII receptor antagonists. Example of these compounds are claimed in EP 253310, EP 323841, EP 324377, EP 409332, EP 411507, EP 412594 A, EP 419048 A.

SUMMARY OF THE INVENTION

The present invention relates to heterocyclic derivatives having AII antagonist properties which may be therefore used for the treatment of different cardiovascular pathologies such as hypertension, heart failure and intraocular hypertension. The compounds of the invention have the general formula I

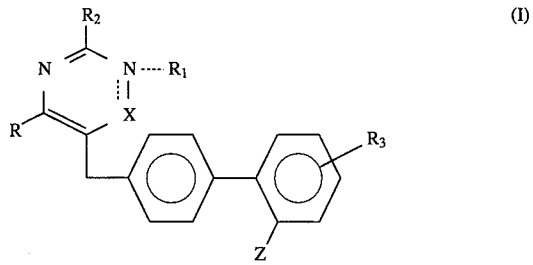

wherein:

R is $C_{1-4}$ linear or branched alkyl;

$R_1$ is hydrogen; $C_{1-4}$ linear or branched alkyl; aryl or arylalkyl wherein aryl is phenyl, naphthyl, 2-thienyl, 2-furanyl optionally substituted by one or more halogens, $C_{1-4}$ alkyl, $C_{1-4}$ alkoxy, hydroxy, carboxy or $C_{1-4}$ linear or branched alkoxycarbonyl groups; when N and X are connected by a double bond, $R_1$ is obviously not present;

$R_2$ is hydrogen, $C_{1-4}$ linear or branched alkyl, hydroxy, amino, aryl, wherein aryl is as defined above, or a group of formula NHA wherein A is $C_2-C_7$ acyl, CN, $NO_2$, CONHB or CSNHB wherein B is hydrogen, $C_1-C_4$ linear or branched alkyl, $C_{3-7}$ cycloalkyl, aryl as defined above;

$R_3$ is hydrogen or one o more halogen atoms;

X is CO or a C—$R_4$ group wherein $R_4$ may be $OR_1$ (wherein $R_1$ must be obviously present and has the above mentioned meanings), aryl optionally substituted by carboxy or hydroxy groups or $CH_2OR_5$ wherein $R_5$ is hydrogen, lower alkyl, arylalkyl wherein the aryl portion is as defined above;

Z is a $COOR_6$ group wherein $R_6$ is hydrogen or $C_{1-4}$ linear or branched alkyl or a tetrazol-5-yl group of formula

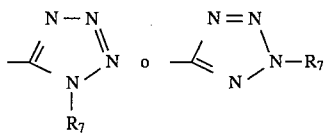

wherein $R_7$ is hydrogen or $C_{1-4}$ alkyl with the proviso that, when X is CO and $R_1$=H, phenyl or phenethyl, $R_2$ is different from hydrogen or alkyl.

The disclaimed compounds are known from EP 0435827.

Preferred compounds of formula I are those wherein X is CO;

$R_1$ is preferably hydrogen; $C_1-C_4$ alkyl; phenyl, benzyl, thienyl or furanyl optionally substituted by carboxy or $C_1-C_4$ alkoxycarbonyl groups;

$R_2$ is preferally hydrogen; $C_1-C_4$ alkyl; amino; phenyl, 2-thienyl, 2-furanyl optionally substituted by carboxy or $C_1-C_4$ alkoxycarbonyl groups;

$R_3$ is preferably hydrogen.

Another group of preferred compounds, is that where $R_2$ is hydrogen or $C_{1-4}$ alkyl and $R_1$ is $C_{1-4}$ alkyl, phenyl, benzyl, furanyl or thienyl optionally, substituted by carboxy or alkoxy carbonyl group. Particularly preferred are the compounds wherein $R_2$ is amino. Particularly preferred compounds are: 4-butyl-1-[(2-carboxyphenyl) methyl]-2-methyl-5-[[2'-(1H-tetrazol-5-yl) biphenyl-4-]methyl]pyrimidin-6-one and 2-amino-6-butyl-5-[[2'-(1H-tetrazol-5-yl) biphenyl-4-yl]methyl]-pyrimidin-4-one.

The compounds I are characterized by a methylbiphenyl group on a carbon atom instead of a nitrogen atom as in the prior art.

The invention relates also the pharmaceutically acceptable salts of the compounds I with organic or inorganic bases or acids. These salts include ammonium salts, alkali metal salts such as sodium and potassium, alkaline-earth metal salts such as calcium and magnesium, organic bases salts, e.g. with dicyclohexylamine, N-methyl-D-glucamine, with aminoacids such as arginine, lysine and so on. Examples of salts with organic or inorganic acids, are those with hydrochloric, hydrobromide, sulfuric, phosphoric, methanesulfonic, toluensulfonic, maleic, fumaric, camphorsulfonic acids, etc.

The invention relates also to the process for the preparation of the compounds I.

The compounds of formula I wherein Z is a $COOR_6$ group ($R_6$ is a $C_{1-4}$ alkyl) or a substituted tetrazolyl group, are prepared by reacting a 1,3-dicarbonyl derivative or a B-ketoacid derivative of formula II

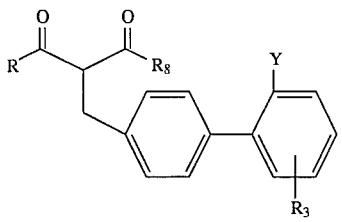

wherein:

R and $R_3$ are as defined for the formula I $R_8$ is an $OR_9$ group ($R_9$ is methyl or ethyl) or a $CH_2OR_5$ group wherein $R_5$ is as defined for the formula I Y is $COOR_6$ group ($R_6$ is $C_{1-4}$ alkyl group) or a substituted tetrazol-5-yl group, with compounds of formula III

wherein $R_1$ and $R_2$ are as defined for the formula X, with the proviso that $R_1$ is at least hydrogen.

The reaction is carried out in a protic solvent such as a lower alcohol (e.g. methanol, ethanol, isopropansi) or in water or in mixtures there of or in an aprotic solvent such as benzene or toluene, optionally in the presence of bases such as an alcoholate ($CH_3ONa$, $C_2H_5ONa$, ter-ButOK), an alkali or alkaline-earth metal hydroxide or carbonate. The temperature may range from the room temperature to the reflux temperature.

The formation of the heterocycle may be carried out also in the presence of acids such as acetic acid or hydrochloric acid, at a temperature from 20° to 80° C. Alternatively, the compounds I are prepared starting from compounds of formula IV

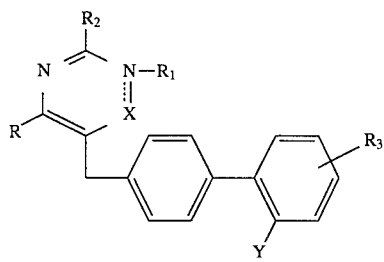

wherein:

R, $R_1$, $R_2$ and $R_3$ are as defined above

Y is a $COOR_6$ group ($R_6$ being a $C_{1-4}$ alkyl), CN or a tetrazol-5-yl group substituted by a triphenylmethyl group.

When Y is an alkoxycarbonyl group, the compound IV may be subjected to acid (i.e. hydrochloric; trifluoroacetic, formic, acetic acids in protic solvents such as water-alcohol mixtures or in aprotic solvents such as $CH_2Cl_2$, dioxane) or alkaline (alkali hydroxides in water-alcohol mixtures at temperatures from 20° to 80 ° C.) hydrolysis.

When Y is a CN group, it may be hydrolyzed with strong acids or bases, preferably with 1:1 aqueous hydrochloric acid and glacial acetic acid mixture at reflux, or with NaOH in ethanol or ethylene glycol at temperatures from 20° to the reflux temperature. The CN group may be converted into the tetrazolyl derivative by treatment with $NaN_3$ and $NH_4Cl$ in DMF at temperatures from 30 to 120 ° C., or by 1,3-dipolar addition of trialkyl or triaryl stannyl azides in solvents such as toluene o xylene at temperatures from 110° to 130° C.

When Y is a tetrazole group protected by a triphenylmethyl group, the latter may be removed by treatment with acetic, trifluoroacetic or hydrochloric acid or by hydrogenolysis.

The compounds IV wherein $R_1$ is hydrogen may be alkylated in the presence of bases such as $K_2CO_3$, NaH, $NaNH_2$, butillithium, LDA in aprotic polar solvents such as DMF, DMSO, THF at temperature from <20° to +30° Cm with compounds of formula V $$X-CH_2-R_1 \qquad (V)$$

wherein:

$R_1$ is as defined above and X is a leaving groups such as chlorine, bromine, iodine or a mesylate or tosylate groups.

The compounds IV wherein X is $C-R_4$ wherein $R_4$ is $CH_2OCH_2$-phenyl may be transformed into the corresponding hydroxy derivatives by catalytic hydrogenolysis in a hydroxylated solvent such as methanol, ethanol in the presence of platinum or palladium as a catalyst.

The compounds IV are prepared by reacting compounds II wherein Y is as defined for the formula IV, with compounds III according to the previously reported method.

Compounds II are obtained by alkylating known diketones or S-ketoesters, as according to the examples.

The compounds herein described have antagonist activity at AII receptor.

In vitro (inhibition of AII-induced contraction in rabbit aorta and $^{125}I-Sar^1-Ile^8$-AT II displacement in rat adrenal cortex) and in vivo test (inhibition of A II induced pressure response in normotensive rat under ganglionic block).

The compounds of the invention proved to be active in the above tests; for example in the in vitro test on rabbit aorta, several compounds showed $pA_2$ higher than 6,5.

The compounds I or the pharmaceutically acceptable salts thereof con be used in pharmaceutical compositions alone or in admixture with pharmaceutically acceptable adjutants, for oral or parenteral administration. The pharmaceutical compositions can be in the solid form, such as tablets, capsules or suppositories or in the liquid form, such as solutions, suspensions or emulsions.

Further, when parenterally administered, the pharmaceutical composition can be in the form of sterile solutions.

The compounds I can be administered in unitary doses ranging from 1 to 100 mg to patients suffering from cardiovascular pathologies such as hypertension, acute or chronic cardiac failure, intraocular hypertension. The use in other pathologies, such as secondary hyperaldosteronism, pulmonary hypertension, renal disease (glomerulonephritis, diabetic nephropaty) or vascular disorders (hemicrania, Raynaud's syndrome) may also be possible.

The following examples further illustrate the invention.

M.p. are uncorrected; the structure and purity of the compounds were assessed by elementary analysis (C, H, N) and UV, IR, NMR and mass spectroscopy.

Flash chromatography (FC) was carried out on silica gel according to the method described in W. C. Still, J. Org. Chem. 43, 2923 (1978).

EXAMPLE 1

1-Benzyloxy-2,4-octadione

Under nitrogen atmosphere, 0,9 g of $CH_3ONa$, followed after 10 minutes by 2 ml of 2-hexanone, were added to a solution containing 4,9 g of methyl benzyloxyacetate in 50 ml of anhydrous toluene. After stirring for 10 hours at room temperature, 10 ml of water were added and acetic acid was added to pH 5. The toluenic phase was separated and the aqueous phase was extracted with ethyl acetate. The organic phases, pooled with the toluene phase, were washed with a NaC saturated solution, dried over $Na_2SO_4$ and evaporated to dryness. The residue was purified by FC (eluent: hexane/ AcOEt 9:1). 2.5 g of a pale yellow oil were obtained (yield 63%); $^1$H-NMR (200 MHz, CDCl$_3$)δ: 0.92 (t, 3H), 1.22–1.68 (m, 4H), 2.33 (t, 2H), 4.07 (s, 2H), 4.60 (s, 2H), 5.85 (s, 1H), 7.30–7.45 (m, 5H).

Similarly, the following compounds were prepared:

1-benzyloxy-2,4-heptadione;

1-methoxy-2,4-octadione;

1-methoxy-2,4-heptadione;

1-[(4-methoxycarbonylphenyl)methoxy]-2,4-octadione.

EXAMPLE 2

1-Benzyloxy-3-[(2'-methoxycarbonylbiphenyl-4-yl) methyl]-2,4-octadione

Under nitrogen atmosphere, 1.3 g of 1-benzyloxy-2,4-octadione, dissolved in 5 ml of anhydrous DMF were dropped into a suspension containing 0.16 g of 80% NaH in 15 ml of anhydrous DMF. After effervescence was over, 2 g of NaI were added and 1.6 g of 4-bromomethyl-2'-methoxycarbonylbiphenyl, dissolved in 5 ml of anhydrous DMF, were added dropwise to the mixture. After stirring for 6 hours at room temperature and for 6 hours at 70° C., the solvent was evaporated, the residue was treated with H$_2$O and extracted with Et$_2$O. The organic phase was washed with a NaCl saturated solution, dried on Na$_2$SO$_4$ and evaporated to dryness. The residue was purified by FC (eluent: hexane/AcOEt 75:25). 1.3 g of a pale yellow oil were obtained (yield 52%); $^1$H-NMR (200 MHz, CDCl$_3$)δ: 0.80 (t, 3H), 1.08–1.50 (m, 4H), 2.17 (dt, 1H), 2.47 (dt, 1H), 3.02 (dd, 1H), 3.22 (dd, 1H), 3.62 (s, 3H), 3.99 (s, 2H), 4.19 (t, 1H), 4.48 (s, 2H), 7.10–7.55 (m, 12H), 7.82 (dd, 1H).

Similarly, the following compounds were prepared:

1-benzyloxy-3-[(2'-methoxycarbonylbiphenyl-4-yl) methyl]-2,4-heptadione;

1-methoxy-3-[(2'-methoxycarbonylbiphenyl-4-yl)methyl]-2,4-octadione;

1-[(4-methoxycarbonylphenyl)methoxy]-3-[(2'-methoxycarbonylbiphenyl-4-yl) methyl]-2,4-octadione;

1-benzyloxy-3-[(2'-cyanobiphenyl-4-yl)methyl]-2,4-octadione;

1-benzyloxy-3-[[2'- [N-triphenylmethyl- (1H-tetrazol-5-yl)]biphenyl-4-yl]-methyl]-2,4-octadione

EXAMPLE 3

Methyl 3-oxoheptanoate

Under nitrogen atmosphere, 59 ml of butyllithium 1.6M in hexane were added to a solution containing 14 ml of diisopropylamine in 200 ml of anhydrous THF, at After stirring for 20 minutes, 9.3 ml of methyl acetoacetate were dropped, stirring was continued for 30 minutes at 0° C. and further 54 ml of butyllithium 1.6M in hexane were dropped. After further 30 minutes 8.4 ml of propyl iodide were dropped into the dark orange solution. The temperature was allowed to raise to room temperature and after 30 minutes, 50 ml of 37% HCl diluted with 100 ml of H$_2$O were continuously dropped while keeping the temperature under 15° C. The reaction mixture was extracted with Et$_2$O. The organic phase was washed with a NaCl saturated solution, dried on Na$_2$SO$_4$ and evaporated to dryness. The residue was purified by FC (eluent: AcOEt/hexane 1:9). 8.3 g of a clear oil were obtained (yield 61%); $^1$H-NMR (200 MHz, CDCl$_3$)δ: 0.90 (t, 3H), 1.22–1.65 (m, 4H), 2.53 (t, 2H), 3.44 (s, 2H), 3.73 (s, 3H).

Similarly, methyl 3-oxohexanoate was prepared.

EXAMPLE 4

Methyl 2-[(2'-Methoxycarbonylbiphenyl-4-yl)methyl]-3-oxoheptanoate

Under nitrogen atmosphere, 2.3 of methyl 3-oxoheptanoate, dissolved into 10 ml of anhydrous THF were dropped into a suspension containing 0.22 g of 80% NaH in 30 ml g of anhydrous THF. After the effervescence was over, 2.22 g of 4-bromomethyl-2'-methoxycarbonylbiphenyl, dissolved in 10 ml of anhydrous THF, were slowly dropped into the clear solution. After 15 minutes, water was added and acetic acid was added till acidic pH. The reaction mixture was extracted with AcOEt. The organic phase was washed with a NaCl saturated solution, dried on Na$_2$SO$_4$ and evaporated to dryness. The residue was purified by FC (eluent: hexane/AcOEt 8:2). 2.6 g of a clear oil were obtained (yield 93%); $^1$H-NMR (200 MHz, CDCl$_3$)δ: 0.86 (t, 3H), 1.15–1.62 (m, 4H), 2.25–2.65 (m, 2H), 3.20 (d, 2H), 3.63 (s, 3H), 3.71 (s, 3H), 3.84 (t, 1H), 7.12–7.58 (m, 7H), 7.78 (dd, 1H).

Similarly, the following compounds were prepared:

methyl 2-[(2'-cyanobiphenyl-4-yl)methyl]-3-oxoheptanoate; $^1$H-NMR (CDCl$_3$)δ: 0.85 (t, 3H), 1.15–1.63 (m, 4H), 2.27–2.67 (m, 2H), 3.22 (d, 2H), 3.71 (s, 3H), 3.85 (t, 1H), 7.23–7.79 (m, 8H);

methyl 2-[[2'-[N-triphenylmethyl- (1H-tetrazol-5-yl)]biphenyl-4-yl]-methyl]-3-oxoheptanoate; $^1$H-NMR (CDCl$_3$)δ: 0.84 (t, 3H), 1.12–1.61 (m, 4H), 2.18–2.62 (m, 2H), 3.06 (d, 2H), 3.66 (s, 3H), 3.69 (t, 1H), 6.81–7.52 (m, 22H), 7.90 (dd, 1H);

methyl 2-[(2'-methoxycarbonylbiphenyl-4-yl)methyl]-3-oxohexanoate;

methyl 2-[(5'-chloro-2'-methoxycarbonylbiphenyl-4yl)methyl]-3-oxoheptanoate;

methyl 2-[(2'-terbutoxycarbonylbiphenyl-4-yl)methyl]-3-oxoheptanoate.

EXAMPLE 5

6-Butyl-5-[(2'-methoxycarbonylbiphenyl-4-yl)methyl] pyrimidin-4-one

Under nitrogen atmosphere and while cooling, 0.18 g of formamide hydrochloride, followed by 0.87 g of methyl 2-[(2'-methoxycarbonylbiphenyl-4-yl)methyl]-3-oxoheptanoate dissolved into 2 ml of anhydrous MeOH, were added to a solution containing 0.37 g of CH$_3$ONa in 8 ml of anhydrous MeOH.

After stirring for 20 hours at room temperature, the solvent was evaporated, the residue was dissolved in H$_2$O and pH was adjusted to 5 with diluted HCl. The aqueous phase was extracted with Et$_2$O and the white solid, which had separated at the interphase, was filtered off. 0.45 g of product was obtained (yield 53%; m.p.=135°–137° C.).

Similarly, the following compounds were prepared:

5-[(2'-methoxycarbonylbiphenyl-4-yl)methyl]-6-propylpyrimidin-4-one;

6-butyl-5-[(2'-methoxycarbonylbiphenyl-4-yl)methyl]-2-methylpyrimidin-4-one (m.p.=144°–147° C.);

4-benzyloxymethyl-6-butyl-5-[(2'-methoxycarbonylbiphenyl-4-yl) methyl]-2-methylpyrimidine;

4-butyl-5-[(2'-methoxycarbonylbiphenyl-4-yl)methyl]-6-methoxymethyl-2-methylpyrimidine;

4-butyl-5-[(2'-methoxycarbonylbiphenyl-4-yl)methyl]-6-[(4-methoxycarbonylphenyl) methoxymethyl]-2-methylpyrimidine;

6-butyl-5-[(2'-cyanobiphenyl-4-yl)methyl]pyrimidin-4-one;

6-butyl-5-[[2'-[N-triphenylmethyl-(1H-tetrazol-5-yl)]biphenyl-4-yl]methyl]pyrimidin-4-one;

2-amino-6-butyl-5-[(2'-methoxycarbonylbiphenyl-4-yl)methyl]pyrimidin-4-one (m.p. −252°–254° C.);

6-butyl-2-hydroxy-5-[(2'-methoxycarbonylbiphenyl-4-yl)methyl]pyrimidin-4-one;

6-butyl-[(5'-chloro-2'-methoxycarbonylbiphenyl-4-yl)methyl]pyrimidin-4-one;

6-butyl-2-cyanoamino-5-[(2'-methoxycarbonylbiphenyl-4-yl)methyl]pyrimidin-4-one (m.p. 222°–224° C.);

6-butyl-5-[(2'-methoxycarbonylbiphenyl-4-yl)methyl]-2-nitroaminopyrimidin-4-one;

6-butyl-2-methyl-5-[[2'-[N-triphenylmethyl-(1H-tetrazol-5-yl)]biphenyl-4-yl]methyl]pyrimidin-4-one (m.p. 98°–100° C.);

2-amino-6-butyl-5-[[2'-[1H-tetrazol-5-yl)biphenyl-4-yl]methyl]pyrimidin-4-one (m.p. 234°–236° C.).

EXAMPLE 6

4-Butyl-6-hydroxymethyl-2-methyl-5-[(2'-methoxycarbonylbiphenyl-4-yl)methyl]pyrimidine A solution containing 0.5 g of 4-benzyloxymethyl-6-butyl-2-methyl-5-[(2'-methoxycarbonylbiphenyl-4-yl)methyl]pyrimidine in 50 ml of EtOH was hydrogenated in presence of 0.1 g of 10% palladium on charcoal at atmospheric pressure and room temperature. After the theoretical hydrogen absorption the reaction mixture was filtered on Celite® and the solvent was evaporated obtaining 0.38 g of a clear oil, which was directly used without further purification (yield 95%).

EXAMPLE 7

6-Butyl-5-[(2'-carboxybiphenyl-4-yl)methyl]pyrimidin-4-one 0.13 g of NaOH dissolved in 2 ml of $H_2O$ were added to a solution containing 0.42 g of 6-butyl-5-[(2'-methoxycarbonylbiphenyl-4-yl) methyl]pyrimidin-4-one in 10 ml of MeOH. After refluxing for 24 hours under stirring the solvent was evaporated. The residue was dissolved in $H_2O$ and extracted with $Et_2O$. The aqueous phase was acidified to pH 3. The so obtained waxy solid was treated with a $H_2O/Et_2O$ mixture. After filtering, 0.35 g of a white solid was obtained (yield 88%; m.p.=197°–200° C.).

Similarly, the following compounds were prepared:

5-[(2'-carboxybiphenyl-4-yl)methyl]-6-propylpyrimidin-4-one;

6-butyl-5-[(2'-carboxybiphenyl-4-yl)methyl]-2methylpyrimidin-4-one (m.p. −208°–210° C.);

4-butyl-5-[(2'-carboxybiphenyl-4-yl)methyl]-6-hydroxymethyl-2-methylpyrimidine;

4-butyl- 5-[(2'-carboxybiphenyl-4-yl)methyl]-2-methyl-6-methoxymethylpyrimidine;

4-butyl-5-[(2'-carboxybiphenyl-4-yl)methyl]-6-[(4-carboxyphenyl)methoxymethyl]pyrimidine;

2-amino-6-butyl-5-[(2'-carboxybiphenyl-4-yl)methyl]pyrimidin-4-one (m.p. 190°–195° C. dec.);

6-butyl-5-[(2'-carboxybiphenyl-4-yl)methyl]-2-hydroxypyrimidin-4-one;

4-butyl-5-[(2'-carboxybiphenyl-4-yl)methyl]-1-[(4-carboxyphenyl) methyl]pyrimidin-6-one (m.p. 141°–144° C.);

1-benzyl-4-butyl-5-[(2'-carboxybiphenyl-4-yl)methyl]pyrimidin-6-one (m.p. 198°–200° C.);

4-butyl-5-[(2'-carboxybiphenyl-4-yl)methyl]-1-[(4-hydroxyphenyl) methyl]pyrimidin-6-one;

6-butyl-5-[(2'-carboxy-5'-chlorobiphenyl-4-yl)methyl]pyrimidin-4-one.

4-butyl-5-[(2'-carboxybiphenyl-4-yl)methyl]-6-[(3-carboxythien-2-yl) methoxy]-2-methylpyrimidine (m.p. 180°–185° C. dec.);

4-butyl-5-[(2'-carboxybiphenyl-4-yl)methyl]-6-[(3carboxyfuran-2-yl) methyl]-2-methylpyrimidine (m.p. 149°–152° C.) ;

4-butyl-5-[(2'-carboxybiphenyl-4-yl)methyl]-1-[(2carboxyphenyl)methyl]pyrimidin-6-one (m.p. 185°–187° C.);

4-butyl-5-[(2'-carboxybiphenyl-4-yl)methyl]-1-[(3carboxythien-2-yl) methyl]- 2-methylpyrimidin-6-one (m.p. 175°–178° C. dec.);

4-butyl-5-[(2'-carboxybiphenyl-4-yl)methyl]-1-[(3-carboxyfuran-2-yl) methyl]-2-methylpyrimidin-6-one (m.p. 143°–148° C. dec.);

4-butyl-5-[(2'-carboxybiphenyl-4-yl)methyl]-1-[(thien-2-yl) methyl]pyrimidin-6-one (m.p. 205°–208° C.);

6-butyl-5-[(2'-carboxybiphenyl-4-yl)methyl]-2-cyanoaminopyrimidin-4-one (m.p. 230°–232° C.);

6-butyl-5-[(2'-carboxybiphenyl-4-yl)methyl]-2-nitroaminopyrimidin-4-one;

6-butyl-5-[(2'-carboxybiphenyl-4-yl)methyl]-2-phenylaminocarbonylaminopyrimidin-4-one (m.p. 229°–231° C.);

6-butyl-5-[(2'-carboxybiphenyl-4-yl)methyl]-2-cyclohexylaminocarbonylaminopyrimidin-4-one (m.p. 234°–236° C.);

6-butyl-5-[(2'-carboxybiphenyl-4-yl)methyl]-2-methylaminothiocarbonylaminopyrimidin-4-one (m.p. 179°–181° C.);

2-aminocarbonylamino-6-butyl-5-[(2'-carboxybiphenyl-4-yl)methyl]pyrimidin-4-one;

4-butyl-1-[(3-carboxythien-2-yl)methyl]-5-[[2'-(1H-tetrazol-5-yl) biphenyl-4-yl]methyl]pyrimidin-6-one (m.p. 154°–156° C.);

4-butyl-1-[(3-carboxyfuran-2-yl)methyl]-5-[[2'-(1H-tetrazol-5-yl) biphenyl-4-yl]methyl]pyrimidin-6-one;

4-butyl-5-[(2'-carboxybiphenyl-4-yl)methyl]-6-[[4-carboxyphenyl)methyl]pyrimidine (m.p. 208°–211° C.).

EXAMPLE 8

43-butyl-5-[(2'-methoxycarbonylbiphenyl-4-yl)methyl]-1-[(4-methoxycarbonylphenyl) methyl]pyrimidin-6-one 0.6 g of 6-butyl-5-[(2'-methoxycarbonylbiphenyl-4-yl)methyl]pyrimidin-4-one dissolved in 3 ml of anhydrous DMF was added to a suspension containing 0.05 g of 80% NaH in 5 ml of anhydrous DMF, while stirring at room temperature. After the effervescence was over, 0.7 ml of methyl 4-bromomethylbenzoate, dissolved in 2 ml of anhydrous DMF, was dropped. After stirring of 3 hours, the solvent was evaporated and the residue was purified by FC (eluent: AcoEt-hexane 1:1). 0.7 g of a clear oil was obtained (yield 85%); $^1$H-NMR (200 MHz, $CDCl_3$)δ: 0.91 (t, 3H), 1.15–1.65 (m, 4H), 2.62 (t, 2H), 3.62 (s, 3H), 3.91 (s, 3H), 3.97 (s, 2H), 5.15 (s, 2H), 7.12–7.52 (m, 9H), 7.78 (dd, 1H), 7.98–8.10 (m, 2H), 8.07 (s, 1H).

Similarly, the following compounds were prepared:

benzyl-4-butyl-5-[(2'-methoxycarbonylbiphenyl-4-yl)methyl]pyrimidin-6-one; ¹H-NMR (CDCl₃)δ: 0.91 (t, 3H), 1.20–1.65 (m, 4H), 2.61 (t, 2H), 3.61 (s, 3H), 3.98 (s, 2H), 5.10 (s, 2H), 7.15–7.52 (m, 12H), 7.78 (dd, 1H), 8.05 (s, 1H);

4-butyl-1-[(4-hydroxyphenyl)methyl]-5-[(2'-methoxycarbonylbiphenyl-4-yl)-methyl]pyrimidin-6-one;

4-butyl-5-[(2'-methoxycarbonylbiphenyl-4-yl)methyl]-1-[(2-methoxycarbonylphenyl) methyl]pyrimidin-6-one; ¹H-NMR (CDCl₃)δ: 0.91 (t, 3H), 1.25–1.65 (m, 4H), 2.63 (t, 2H), 3.61 (S, 3H), 3.91 (s, 3H), 3.97 (s, 2H), 5.55 (s, 2H), 7.12–7.57 (m, 10H), 7.78 (dd, 1H), 8.03 (dd, 1H), 8.15 (S, 1H);

4-butyl-5-[(2'-methoxycarbonylbiphenyl-4-yl)methyl]-1-[(thien-2-yl) methyl]pyrimidin-6-one; ¹H-NMR (CDCl) δ: 0.96 (t, 3H) 1.15–1.65 (m, 4H), 2.60 (t, 2H), 3.62 (s, 3H), 3.98 (s, 2H), 5.25 (s, 2H), 6.89 (dd, 1H), 7.08–7.53 (m, 9H), 7.78 (dd, 1H), 8.08 (s, 1H);

4-butyl-5-[(2'-methoxycarbonylbiphenyl-4-yl)methyl]-1-[(3-methoxycarbonylthien-2-yl) methyl]-2-methylpyrimidin-6-one; ¹H-NMR (CDCl)δ: 0.90 (t, 3H), 1.20–1.65 (m, 4H), 2.47 (s, 3H), 2.58 (t, 2H), 3.61 (s, 3H), 3.90 (s, 3H), 3.99 (s, 2H), 5.91 (s, 2H), 7.08–7.53 (m, 9H), 7.78 (dd, 1H);

4-butyl-5-[(2'-methoxycarbonylbiphenyl-4-yl)methyl]-1-[(3-methoxycarbonylfuran-2-yl) methyl]-2-methylpyridin-6-one; ¹H-NMR (CDCl₃)δ: 0.90 (t, 3H), 1.15–1.65 (m, 4H), 2.47 (s, 3H), 2.57 (t, 2H), 3.61 (s, 3H), 3.88 (s, 3H), 3.98 (s, 2H), 5.69 (s, 2H), 6.69 (d, 1H). 7.12–7.55 (m, 8H), 7.78 (dd, 1H);

4-butyl-1-[(2-methoxycarbonylbiphenyl)methyl]-2-methyl-5-[[2'-[N-triphenylmethyl-(1H-tetrazol-5-yl) ]biphenyl-4-yl]methyl]pyrimidin-6-one; ¹H-NMR (CDCl₃)δ: 0.91 (t, 3H), 1.15–1.65 (m, 4H), 2.36 (s, 3H), 2.53 (t, 2H), 3.85 (s, 2H), 3.93 (s, 3H), 5.73 (s, 2H), 6.75 (dd, 1H), 6.82–7.10 (m, 8H) 7.18–7.48 (m, 16H), 7.78 (dd, 1H), 8.08 (dd, 1H);

4-butyl-1-[(3-methoxycarbonylthien-2-yl)methyl]-2-methyl-5-[[2'-[N-triphenylmethyl-(1H-tetrazol-5-yl) ]biphenyl-4-yl]methyl]pyrimidin-6-one; ¹H-NMR (CDCl₃)δ: 0.88 (t, 3H), 1.20–1.65 (m, 4H), 2.46 (s, 3H), 2.50 (t, 2H), 3.86 (s, 2H), 3.90 (s, 3H), 5.87 (s, 2H), 6.80–7.55 (m, 24H) 7.88 (dd, 1H);

4-butyl-1-[(3-methoxycarbonyl furan-2-yl)methyl]-2-methyl-5-[[2'-[N-triphenylmethyl-(1H-tetrazol-5-yl) ]biphenyl-4-yl]methyl]pyrimidin-6-one; ¹H-NMR (CDCl₃)δ: 0.90 (t, 3H), 1.15–1.65 (m, 4H), 2.46 (s, 3H), 2.50 (t, 2H), 3.86 (s, 2H), 3.88 (s, 3H), 5.66 (s, 2H), 6.69 (d, 1H), 6.80–7.55 (m, 23H) 7.88 (dd, 1H);

4-butyl-1-[(4-methoxycarbonylphenyl) methyl]-2-methyl-5 -[[2'-[N-triphenylmethyl-(1H-tetrazol-5-yl) ]biphenyl-4-yl]methyl]pyrimidin-6-one; ¹H-NMR (CDCl₃)δ: 0.91 (t, 3H), 1.15–1.65 (m, 4H),2.36 (s, 3H), 2.53 (t, 2H), 3.85 (s, 2H), 3.93 (s, 3H), 5.33 (s, 2H), 6.75 (dd, 1H), 6.82–7.10 (m, 8H) 7.18–7.48 (m, 16H), 7.78 (dd, 1H), 8.08 (dd, 1H);

4-butyl-5-[(2'-methoxycarbonylbiphenyl-4-yl)methyl]-6-[(4-methoxycarbonylphenyl) methoxy]pyrimidine; 1HNMR (CDCl)δ: 0.91 (t, 3H), 1.20–1.70 (m, 4H), 2.77 (t, 2H), 3.61 (s, 3H), 3.90 (s, 3H), 4.08 (s, 2H), 5.48 (s, 2H), 7.05–7.55 (m, 9H) 8.81 (dd, 1H), 7.93–8.01 (m, 2H), 8.63 (s, 1H);

4-butyl-5-[(2'-methoxycarbonylbiphenyl-4-yl)methyl]-6-[(2-methoxycarbonylphenyl) methoxy]pyrimidine; 1H-NMR (CDCl)δ: 0.91 (t, 3H), 1.20–1.70 (m, 4H), 2.77 (t, 2H), 3.58 (s, 3H), 3.86 (s, 3H), 4.09 (s, 2H), 5.86 (s, 2H), 7.06–7.56 (m, 10H) 7.78 (dd, 1H), 7.98 (dd, 1H), 8.63 (s, 1H);

4-butyl-5-[(2'-methoxycarbonylbiphenyl-4-yl)methyl]-6-[(3-methoxycarbonylthien-2-yl) methoxy]-2methylpyrimidine; ¹H-NMR (CDCl₃)δ: 0.89 (t, 3H), 1.20–1.65 (m, 4H), 2.59 (s, 3H), 2.71 (t, 2H), 3.59 (s, 3H), 3.87 (s, 3H), 4.06 (s, 2H), 5.96 (S, 2H), 7.12–7.52 (m, 9H) 7.78 (dd, 1H);

4-butyl-5-[(2'-methoxycarbonylbiphenyl-4-yl)methyl]-6-[(3-methoxycarbonylfuran-2-yl) methoxy]-2-methylpyrimidine; ¹H-NMR (CDCl₃)δ: 0.88 (t, 3H), 1.20–1.65 (m, 4H), 2.58 (s, 3H), 2.65 (t, 2H), 3.60 (s, 3H), 3.81 (s, 3H), 3.96 (s, 2H), 5.71 (s, 2H), 6.72 (d, 1H), 7.02–7.55 (m, 8H), 7.78 (dd, 1H);

4-butyl-6-[(4-methoxycarbonylphenyl) methoxy]-2-methyl -5-[[2'-[N-triphenylmethyl-(1H-tetrazol-5-yl) ]biphenyl-4-yl]methyl]pyrimidine; ¹H-NMR (CDCl₃) δ: 0.86 (t, 3H), 1.20–1.70 (m, 4H), 2.56 (s, 3H), 2.62 (t, 2H), 3.88 (s, 3H), 3.90 (s, 2H), 5.42 (s, 2H), 6.82–7.03 (m, 8H), 7.15–7.52 (m, 17H), 7.85–8.00 (m, 2H);

4-butyl-6-[(2-methoxycarbonylphenyl)methoxy]-2-methyl-5 -[[2'-[N-triphenylmethyl-(1H-tetrazol-5-yl) ]biphenyl-4-yl]methyl]pyrimidine; ¹H-NMR (CDCl3) δ: 0.86 (t, 3H), 1.15–1.60 (m, 4H), 2.56 (s, 3H), 2.62 (t, 2H), 3.84 (s, 3H), 3.91 (s, 2H), 5.80 (s, 2H), 6.82–7.03 (m, 8H), 7.15–7.52 (m, 17H), 7.85–8.00 (m, 2H);

4-butyl-6-[(3-methoxycarbonylthien-2-yl)methoxy]-2-methyl -5-[[2'-[N-triphenylmethyl-(1H-tetrazol-5-yl) ]biphenyl-4-yl]methyl]pyrimidine; ¹H-NMR (CDCl3) δ: 0.86 (t, 3H), 1.20–1.60 (m, 4H), 2.59 (s, 3H), 2.61 (t, 2H), 3.85 (s, 3H), 3.93 (s, 2H), 5.93 (s, 2H), 6.82–7.48 (m, 24H), 7.87 (dd, 1H);

4-butyl-6-[(3-methoxycarbonyl furan-2-yl)methoxy]-2-methyl -5-[[2'-[N-triphenylmethyl-(1H-tetrazol-5-yl) ]biphenyl-4-yl]methyl]pyrimidine; ¹H-NMR (CDCl3) δ: 0.86 (t, 3H), 1.20–1.60 (m, 4H), 2.55 (s, 2H), 2.59 (s, 3H), 3.80 (s, 3H), 3.85 (s, 2H), 5.69 (s, 2H), 6.70 (d, 1H), 6.80–7.50 (m, 23H), 7.87 (dd, 1H).

EXAMPLE 9

6-Butyl-5-[(2'-(1H-tetrazol-5-yl)biphenyl-4-yl)methyl]pyrimidin-4-one

Method A

Under nitrogen atmosphere, 0.11 g of sodium azide and 0.09 g of ammonium chloride were added to a solution containing 0.2 g di 6-butyl-5-[(2'-cyanobiphenyl-4-yl) -methyl]pyrimidin-4-one in 2 ml of anhydrous DMF. After reacting for 16 hours at 100° C. and 60 hours at 120° C. the reaction mixture was let to cool down and a further amount equal to the former of sodium azide and ammonium chloride was added. After further 50 hours at 120° C. the solid was filtered off and the solvent was distilled under vacuum. The residue was dissolved in H₂O and extracted with AcOEt, the organic phase was dried on Na₂SO₄ and the solvent was evaporated. The crude material was purified by FC (eluent: AcOEt/MeOH) obtaining 12 g of a white solid (yield 53%).

Method B 1 ml of trifluoroacetic acid and 1 ml of H₂O were added to a solution containing 0.3 g of 6-butyl-5-[[2'-[N-triphenylmethyl-(1H-tetrazol-5-yl) ]biphenyl-4-yl]methyl]pyrimidin-4-one in 5 ml of THF. After stirring for 2 hours at room temperature, the reaction mixture was treated with NaOH to neutrality and the solvent was evaporated. The residue was purified by FC, according to Method A. 0.11 g of a white solid was obtained (yield 60%).

Similarly, the following compounds were prepared:

6-butyl-2-methyl-5-[[2'-(1H-tetrazol-5-yl) biphenyl-4-yl] methyl]pyrimidin-4-one (m.p. 238°–240° C. dec.);

1-benzyl-4-butyl-5-[[2'-(1H-tetrazol-5-yl)biphenyl-4-yl] methyl]pyrimidin-6-one;

4-butyl-1-[(2-carboxyphenyl)methyl]-2-methyl-5-[ [2'(1H-tetrazol-5-yl) biphenyl-4-yl]methyl]pyrimidin-6one (m.p. 193°–196° C.);

4-butyl-6-[(2-methoxycarbonylphenyl)methoxy]-2-methyl-5-[[2'-(1H-tetrazol-5-yl) biphenyl-4-yl]methyl]pyrimidine (m.p. 103°–105° C.);

4-butyl-1-[(3-methoxycarbonylthien-2-yl)methyl]-2'-methyl-5-[[2'-(1H-tetrazol-5-yl)biphenyl-4-yl]methyl]-pyrimidin-6-one (m.p. 100°–105° C.);

4-butyl-6-[(3-methoxycarbonylthien-2-yl)methoxy]-2-methyl -5-[[2'-(1H-tetrazol-5-yl) biphenyl-4-yl]methyl]-pyrimidine (m.p. 100°–105° C.);

4-butyl-1-[(3-methoxycarbonylfuran-2-yl)methyl]-2-methyl -5-[[2'-(1H-tetrazol-5-yl)biphenyl-4-yl]methyl]pyrimidin-6-one;

4-butyl-6-[(3-methoxycarbonyl furan-2-yl) methoxy]-2-methyl -5-[[2'-(1H-tetrazol-5-yl) biphenyl-4-yl]methyl]pyrimidine;

4-butyl-1-[(4-carboxyphenyl)methyl]-2-methyl-5-[ [2'(1H-tetrazol-5-yl) biphenyl-4-yl]methyl]pyrimidin-6one;

4-butyl-6-[(4-methoxycarbonylphenyl)methoxy]-2-methyl -5-[[2'-(1H-tetrazol-5-yl) biphenyl-4-yl]methyl] pyrimidine.

EXAMPLE 10

6-Butyl-5-[(2'-methoxycarbonylbiphenyl-4-yl)methyl]-2-phenylaminocarbonylaminopyrimidin-4-one 0.27 g of phenylisocyanate were added to a solution containing 0.3 g of 2-amino-6-butyl-5-[(2'-methoxycarbonylbiphenyl-4-yl) -methyl]pyrimidin-4-one in ml of dry DMF at 0° C. After stirring at room temperature for 30 minutes the mixture was evaporated to dryness and the residue was crystallized from DMF; 0.22 g of a white solid was obtained (yield 56%, m.p. 217°–219° C.).

Similarly, the following compounds were prepared:

6-butyl-2-cyclohexylaminocarbonylamino-5-[(2'-methoxycarbonylbiphenyl-4-yl) methyl]pyrimidin-4-one (m.p. 220°–222° C.);

6-butyl-5-[(2'-methoxycarbonylbiphenyl-4-yl)methyl]-2-methylaminothiocarbonylaminopyrimidin -4-one (m.p. 186°–188° C.);

2-aminocarbonylamino-6-butyl-[(2'-methoxycarbonylbiphenyl-4-yl) methyl]pyrimidin-4-one.

EXAMPLE 11

2-Acetylamino-6-butyl-5-[[2'-(1H-tetrazol-5-yl)biphenyl-4-yl]methyl]pyrimidin-4-one 10 ml of Ac20 were added to a suspension of 2-amino -6-butyl-5-[(2'-(1H-tetrazol-5-yl)biphenyl-4-yl]methyl]pyrimidin-4-one in toluene. After other additions of Ac$_2$O the solution was evaporated to dryness. The residue was purified by FC (eluent: CH$_2$Cl$_2$/MeOH/AcOH 89.9:10:0.1). 15 mg of a white solid was obtained (yield 32%, m.p. 205°–208° C.).

We claim:

1. A compound of formula I

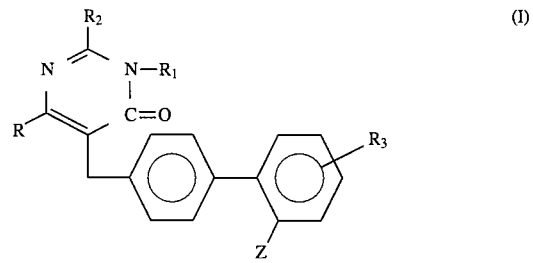

wherein:

R is $C_{1-4}$ linear or branched alkyl;

$R_1$ is aryl-lower alkyl wherein aryl is 2-thienyl or 2-furanyl, said 2-thienyl or 2-furanyl being substituted by $C_{1-4}$ linear or branched alkoxycarbonyl groups; $R_2$ is hydrogen, $C_{1-4}$ linear or branched alkyl, hydroxy, amino, aryl, wherein aryl is as defined hereinabove, or a group of formula NHA wherein A is $C_2$–$C_7$ acyl, CN, $NO_2$, CONHB or CSNHB wherein B is hydrogen, $C_1$–$C_4$ linear or branched alkyl, $C_{3-7}$ cycloalkyl, aryl is as defined hereinabove; $R_3$ is hydrogen or one or more halogen atom; Z is a $COOR_6$ group wherein $R_6$ is hydrogen or $C_{1-4}$ linear or branched alkyl or Z is a tetrazol-5-yl group of formula:

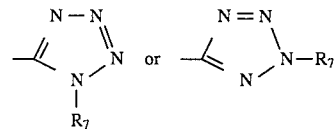

wherein $R_7$ is hydrogen or $C_{1-4}$ alkyl.

2. The compound according to claim 1 which is 4-butyl-1-[(3-carboxythien-2-yl) methyl-5-[[2'-(1H-tetrazol-5-yl)biphenyl-4-yl) methyl]pyrimidin-6-one and a pharmaceutically acceptable salt thereof.

3. The compound according to claim 1 which is 4-butyl-1-[(3-methoxycarbonyl furan-2-yl)methyl]-5-[[2'-(1H-tetrazol-5-yl)-biphenyl-4-yl) methyl]pyrimidin-6-one and a pharmaceutically acceptable salt thereof.

4. The compound according to claim 1 which is 4-butyl-1-[(3-methoxycarbonylthien-2-yl) methyl]-2-methyl-5-[[2'-(1H-tetrazol-5-yl) biphenyl-4-yl]methyl]-pyrimidin-6-one.

5. A pharmaceutical composition containing an effective amount of a compound according to claim 1 as an active ingredient and excipients for oral or parenteral administration in the form of a tablet, a capsule, a suppository, a solution, a suspension or an emulsion.

6. The method of treatment of a living subject affected by a cardiovascular pathology which consists of administering to said living subject a composition containing 1–100 mgs per unit dose of a compound of formula I

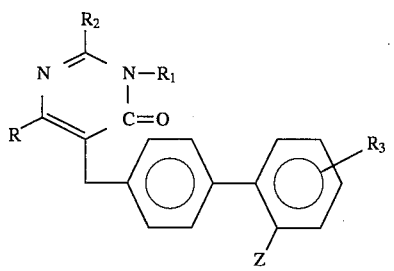 (I)

wherein:

R is $C_{1-4}$ linear or branched alkyl;

$R_1$ is aryl-lower alkyl wherein aryl is 2-thienyl or -furanyl, said 2-thienyl or 2-furanyl being substituted by $C_{1-4}$ linear or branched alkoxycarbonyl groups; $R_2$ is hydrogen, $C_{1-4}$ linear or branched alkyl, hydroxy, amino, aryl, wherein aryl is as defined hereinabove, or a group of formula NHA wherein A is $C_2$–$C_7$ acyl, CN, $NO_2$, CONHB or CSNHB wherein B is hydrogen, $C_1$–$C_4$ linear or branched alkyl, $C_{3-7}$ cycloalkyl, aryl is as defined hereinabove; $R_3$ is hydrogen or one or more halogen atom; Z is a $COOR_6$ group wherein $R_6$ is hydrogen or $C_{1-4}$ linear or branched alkyl or a tetrazol-5-yl group of formula

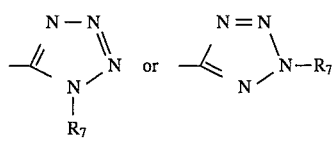

wherein $R_7$ is hydrogen or $C_{1-4}$ alkyl.

* * * * *